United States Patent [19]

Bryan

[11] Patent Number: 4,888,489
[45] Date of Patent: Dec. 19, 1989

[54] HAND-HELD DEVICE FOR CURING A DENTAL RESTORATIVE MATERIAL

[75] Inventor: Thomas T. Bryan, St. Paul, Minn.

[73] Assignee: Minnesota Mining and Manufacturing Company, St. Paul, Minn.

[21] Appl. No.: 191,911

[22] Filed: May 9, 1988

[51] Int. Cl.⁴ .............................................. A61C 13/14
[52] U.S. Cl. ............................ 250/504 H; 250/492.1; 250/503.1; 433/29
[58] Field of Search ............ 250/504 H, 504 R, 492.1, 250/503.1; 433/29, 80, 89, 100

[56] References Cited

U.S. PATENT DOCUMENTS

| Re. 32,073 | 1/1986 | Randklev | 523/177 |
| 3,983,039 | 9/1976 | Eastland | 250/492.1 |
| 4,298,806 | 11/1981 | Herold | 250/504 H |
| 4,385,344 | 5/1983 | Gonser | 362/32 |
| 4,471,226 | 9/1984 | Wisnosky et al. | 250/504 H |
| 4,503,169 | 3/1985 | Randklev | 523/117 |
| 4,623,795 | 11/1986 | Knopp et al. | 250/493.1 |
| 4,648,838 | 3/1987 | Schlachter | 433/29 |

FOREIGN PATENT DOCUMENTS 1544776 of 0000 United Kingdom .

OTHER PUBLICATIONS

Commercial Brochure "A Bright New Generation. Visilux TM 2 From 3M".

Primary Examiner—Jack J. Berman
Attorney, Agent, or Firm—Donald M. Sell; Walter N. Kirn; James D. Christoff

[57] ABSTRACT

When a hand-held visible-light curing unit is used in air to cure dental restorative material, a thin layer of soft, uncured surface material ordinarily remains and is removed by grinding. In the invention, the surface of the restorative material is fully cured by the simple expedient of using a hand-held light curing unit whose lightguide has a hollow tube having at least one orifice that is substantially colinear with the lightguide. An inert gas such as nitrogen is gently blown through the orifice and across the surface of the restorative material while the material is being cured by light from the light curing unit.

12 Claims, 1 Drawing Sheet

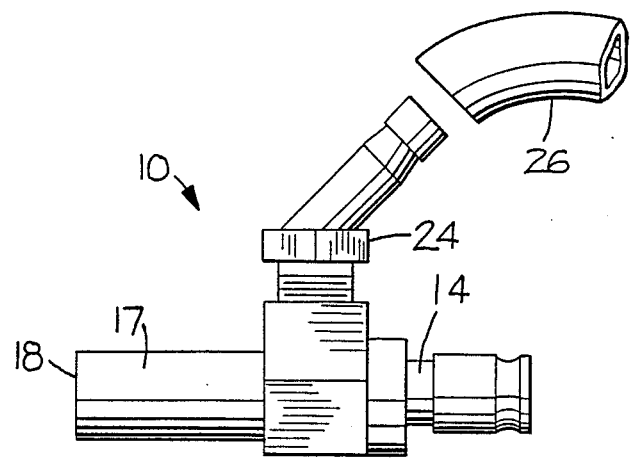
FIG. 1
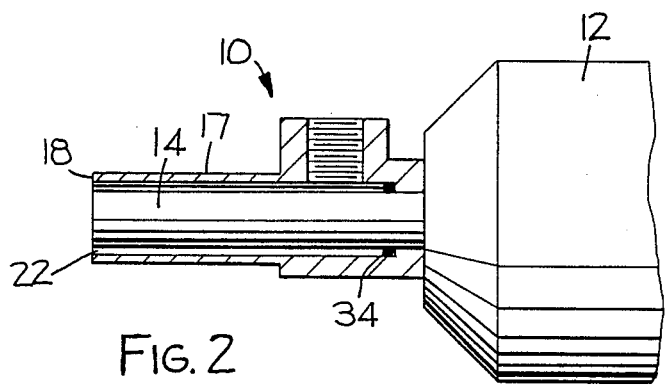
FIG. 2
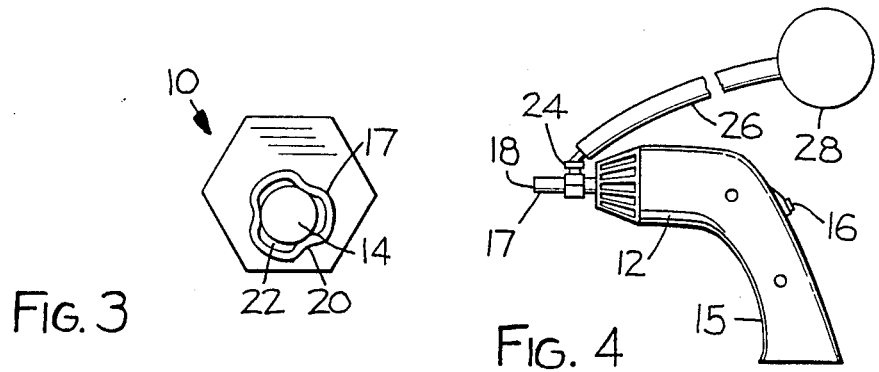
FIG. 3
FIG. 4

HAND-HELD DEVICE FOR CURING A DENTAL RESTORATIVE MATERIAL

BACKGROUND OF THE INVENTION

1. Field of the Invention

The invention is concerned with enhancing the cure of a dental restorative material, especially a photocurable material such as is used for making dental restorations. The invention also has nondental uses such as the restoration of art objects.

2. Description of the Related Art

Modern dental restorative materials typically are based on a plastic binder material and are cured by exposure to radiant energy, usually blue light within the range of 400 to 500 nm. Most such restorative materials contain an acrylate or methacrylate binder material, a filler such as quartz powder, and a photoinitiator. Representative dental restorative materials are described in U.S. Pat. No. 4,503,169 (Randklev), U.S. Pat. No. Re. 32,073 (Randklev), and U.K. Pat. Spec. No. 1,544,776.

Although such restorative mterials cure within a few seconds, air inhibits the cure so that a thin layer of soft, uncured or incompletely cured surface material must be removed by grinding or polishing. This has been avoided by covering the uncured restorative with a thin film that is transparent and impervious to air, e.g., a preformed film such as "Saran" wrap [poly(vinylidene chloride)] or a coating of glycerine. When using a preformed film, it can be difficult and tedious to assure complete coverage; and when using glycerine, some care is required to clean it away. Because of such difficulties, most dentists do not use any covering, but instead use an excess of the restorative material and grind away the excess, even though this takes time and the grinding involves a risk of damaging adjacent tooth surfaces. This also makes it difficult to attain accurate anatomical form, especially at mesio-distal or occlusal contact points.

A photocurable dental restorative material can be cured either in-the-mouth or out-of-the-mouth. For in-the-mouth curing, a hand-held visible light curing unit is used, typically consisting of a handpiece which contains a lamp and from which a fused glass fiber optic lightguide projects, or a desk-mounted light source from which a hand-held flexible fiber optic cable projects. Representative hand-held light curing units include the "Elipar" light from Espe, also shown in U.S. Pat. No. 4,298,806 (Herold); the "Visilux 2" light from 3M; and the light shown in U.S. Pat. No. 4,385,344 (Gonser).

OTHER ART

U.S. Pat. No. 4,471,226 (Wisnosky et al.) concerns a safety housing for portable radiation applicators, especially hand-held ultraviolet lamps. The safety housing includes a lamp, reflector, switches, and a mechanical lock-out device, and due to its size would not be suitable for use in the mouth. The safety housing can be equipped with a pipe "to supply air cooling to the lamp or a gas such as nitrogen to produce an inert atmosphere around the work area. The process of polymerization occurs more satisfactorily in an inert atmosphere" (col 3, lines 27-33). This inert atmosphere would be maintained within the relatively tightly enclosed safety housing.

SUMMARY OF THE INVENTION

The present invention solves the above-discussed problems by the simple expedient of equipping a hand-held visible light curing unit with a hollow tube that will gently blow inert gas across the surface of a restorative material while the material is being cured by being exposed to radiant energy of a wavelength that cures the restorative material. A tightly enclosed safety housing such as is described by Wisnosky et al. is not required. By removing oxygen from the surface, there is no uncured material at the surface of the restoration. A surprisingly small amount of inert gas is required, and suitable gas-blowing apparatus can be provided at very low cost. For optimum results, the inert gas should be mementarily blown across the surface of the restorative material before exposing the material to the radiant energy.

A hand-held device that accomplishes this desirable result includes:
- means for directing radiant energy of a wavelength that cures restorative material, and
- means for directing a gentle flow of inert gas in substantially the same direction as the radiant energy is directed, whereby said gas blows across the surface of said restorative material.

Preferably, the inert gas directing means is provided by a hollow tube enveloping said energy-directing means with an orifice therebetween.

"Inert gas" as used herein means any gas that permits restorative material to cure without leaving uncured surface material. Gases which have proved to be useful and hence can be considered to be "inert" include nitrogen, helium, argon, chlorofluorocarbons such as the "Freon" series from E.I. duPont de Nemours & Co., nitrous oxide, carbon dioxide, and even hydrogen, although the latter is likely to be too hazardous for commercial use. Nitrogen is preferred, since it is inexpensive and free from hazards. Nitrous oxide is also preferred, since it is widely available in dental offices.

THE DRAWING

In the drawing, all figures of which are schematic:
FIG. 1 is a side elevation of a portion of a hand-held device embodying the invention;
FIG. 2 is a fragmentary longitudinal section of FIG. 1;
FIG. 3 is an end view of the device of FIGS. 1 and 2; and
FIG. 4 is a reduced, fragmentary side elevation of the device of FIGS. 1-3.

DETAILED DESCRIPTION

Except for a slip-on attachment to provide a flow of inert gas, the hand-held device 10 shown in FIGS. 1-4 can be made from commercially available airing units such as the "Visilux 2" visible light curing unit (3M). The device 10 has a dome-like housing 12 for a lamp (not shown) that emits visible blue light mainly radiating at 460 nm. Projecting from the center of the dome is a transparent lightguide 14 containing a bundle of optical fibers for collimating light emitted by the lamp. The lightguide 14 is substantially cylindrical, although the lightguide can, if desired, contain one or more gentle bends to direct the light around corners, and the optical fibers afford a corrugated effect at its surface. Integral with the lamp houding 12 is a pistol grip 15 having a trigger switch 16 that controls both the lamp and the flow of inert gas through a thin metal tube 17 of the slip-on attachment enveloping the lightguide 14. With the slip-on attachment in place, the mental tube 17 is coaxial with the lightguide and is coextensive with the lightguide, that is, it ends substantially flush with the distal or outlet end of the lightguide. A shorter or longer tube can be used if desired. The distal end 18 of the tube 17 has three uniformly spaced crimps 20 that rest against the free end of the lightguide to leave an interrupted annular orifice 22 (as seen in FIG. 3) between the lightguide and the tube 17.

As shown in FIG. 1, the slip-on attachment has a fitting 24 on the tube 17 that is connected by a flexible hose 26 to a tank of compressed nitrogen (not shown). At the outlet of the tank is a valve 28 that is electrically controlled from the thumb-actuated switch on the pistol grip of the lamp housing 12. When the switch is actuated to light the lamp and open the valve, nitrogen immediately flows through the hose 26, into the tube 17, and out of the orifice 22 in the same direction as light emitted from the optical fibers in the lightguide 14. The nitrogen is prevented from flowing throught the tube 17 in the opposite direction by a rubber O-ring 34.

Preferably there is an electrical circuit in the lamp housing 12 to delay the lighting of the lamp momentarily until the nitrogen has blown the air away from the photocurable restorative material. Such a delay may accelerate the rate of cure of the restorative material but is not required, because testing shows that the restorative material becomes thoroughly cured in the absence of a delay. When the switch is released, both the lamp and the flow of nitrogen can be immediately turned off, or sequentially turned off in any desired order.

In addition to use in the mouth to cure conventional fillings, the device of the invention can also be used in the mouth to cure sealants, and used in the mouth or outside the mouth to cure veneers, inlays, onlays, crwons and other dental restorations.

The hand-held curing device of the invention, while being primarily useful in making dental restorations, can be put to various diverse uses such as the repair of statues and other art objects.

EXAMPLE 1

Using a dental tooth model having a prepared tooth, namely a "Typodont" model ("R862", Columbia Dentoform) of two molar and two bicuspid teeth, a dental restoration in the form of an inlay 1 cm long and 5 mm in maximum thickness was prepared using a photocurable dental restorative material, namely "Silux" restorative from 3M. A hand-held "Visilux 2" visible light curing unit was converted as shown in FIGS. 1–4 of the drawing. The diameter of the lightguide 14 was 7 mm and the inside diameter of the metal tube 17 was about 1.1 mm. While blowing nitrogen gently through the metal tube 17 and across the restorative material at 50 cm$^3$/min., the material was cured by operating the lamp while holding the output end of the lightguide close to but not touching the restorative material. The extent of cure at the surface of the restoration was evaluated by coating the surface with a 1 weight percent potassium permanganate solution. The absence of any staining by the permanganate solution indicates that the surface had become fully cured.

Results of the permanganate staining test were as follows:

|   | | Staining |
|---|---|---|
| A. | Both light and nitrogen flow maintained for 20 seconds | None |
| B. | Same conditions as A except that nitrogen flow turned off after first 5 sec. | None |
| C. | Same conditions as A except that nitrogen flow turned off after first 2 sec. | Light stain |
| D. | Same conditions as A except without using nitrogen | Heavy stain |

EXAMPLE 2

Example 1 was repeated except substituting nitrous oxide for the nitrogen, and the staining results were identical to those reported in Example 1.

EXAMPLE 3

Example 1 was repeated except replacing the nitrogen with liquid chlorofluorocarbon under presure in a container marked "EFFA" Duster from Ernest F. Fullam Inc., Latham, N.Y. Staining results were the same as those reported in Example 1.

The above examples illustrate the manner in which the invention can be used to cure a dental restorative material. Complete cure of the surface of the restorative takes place, without the use of a reformed transparent film or a coating such as glycerine.

Various modifications and alterations of this invention will be apparent to those skilled in the art without departing from the scope and spirit of this invention and the latter should not be restricted to that set forth herein for illustrative purposes.

I claim:

1. A hand-held device useful for curing a photocurable restorative material, said device comprising
   means for directing radiant energy of a wavelength that cures said material along a direction toward the restorative material, and
   means for directing a gentle flow of inert gas in substantially the same direction as the radiant energy is directed as said radiant energy is directed toward said restorative material, whereby said gas blows across said restorative material.

2. A hand held device useful for curing a photocurable restorative material, said device comprising
   means for directing radiant energy of a wavelength that cures said material, and
   means for directing a gentle flow of inert gas in substantially the same direction as the radiant energy is directed, whereby said gas blows across said restorative material,
   said inert gas directing means comprising a hollow tube enveloping said energy-directing means with at least one orifice therebetween.

3. A device as defined in claim 2 wherein said energy-directing means comprises a lightguide containing a bundle of optical fibers for collimating light emitted by a lamp.

4. A device as defined in claim 3 wherein said hollow tube is part of a slip-on attachment that fits over the lightguide and includes a fitting for connecting the attachment to a supply of inert gas.

5. A device as defined in claim 4 wherein said lightguide is substantially cylindrical and said hollow tube has a thin cylindrical metallic wall which is deformed to provide at least three spaced crimps that rest against the lightguide to leave an interrupted annular orifice between the lightguide and the tube.

6. A device as defined in claim 5 wherein said tube is coextensive with the distal end of the lightguide when the attachment is in place.

7. A hand-held device useful for curing a photocurable restorative material, said device comprising
   means for directing radiant energy of a wavelength that cures said material,
   means for directing a gentle flow of inert gas in substantially the same direction as the radiant energy is directed, whereby said gas blows across said restorative material, and
   means for briefly delaying the initiation of the radiant energy until the inert gas has flowed through the orifice for a preselected period of time.

8. A hand-held device useful for curing a radiation-curable restorative material, said device comprising
   a housing containing a lamp,
   a substantially cylindrical transparent lightguide including a bundle of optical fibers for collimating light emitted by the lamp and directing the light along certain direction, and
   an attachment including a cylindrical tube enveloping the lightguide to leave an interrupted annular orifice therebetween and a fitting for connecting the attachment to a supply of inert gas to permit the gas to flow through the orifice in the same direction as the collimated light is directed.

9. A slip-on attachment for a hand-held light curing unit including a lamp and a lightguide containing a bundle of optical fibers for collimating light emitted by the lamp and directing the light along a certain direction, said attachment comprising
   a hollow tube that fits over the lightguide to leave at least one orifice therebetween and
   a fitting for connecting the attachment to a supply of inert gas to permit the gas to flow through the orifice in the same direction as the collimated light is directed.

10. A slip-on attachment as defined in claim 9 wherein the lightguide is substantially cylindrical and the hollow tube has a thin cylindrical metallic wall which is deformed to provide at least three spaced crimps that rest against the lightguide to leave an interrupted annular orifice between the lightguide and the tube.

11. Method of curing of restorative material to provide a dental restoration, said method comprising the simultaneous or sequential steps of
    (1) gently forcing inert gas to flow across the surface of the restorative material to remove oxygen from the surface, and
    (2) directing at the restorative material in the same direction as the flow of said inert gas, radiant energy of a wavelength that cures the restorative material, thereby providing a restoration that is fully cured at its surface.

12. Method as defined in claim 11 wherein the inert gas is selected from the group consisting of nitrogen and nitrous oxide.

* * * * *